United States Patent [19]

Hardy et al.

[11] 4,267,124
[45] May 12, 1981

[54] PROCESS FOR THE MANUFACTURE OF CARBOXYLIC PERACIDS

[75] Inventors: Nicolas Hardy, Jemeppe-sur-Sambre; Luc Lerot; René Walraevens, both of Brussels, all of Belgium

[73] Assignee: Propylox, Brussels, Belgium

[21] Appl. No.: 24,372

[22] Filed: Mar. 27, 1979

[30] Foreign Application Priority Data

Mar. 28, 1978 [FR] France .................................. 78 09199

[51] Int. Cl.³ .................. C07C 179/10; C07C 179/12
[52] U.S. Cl. ............................. 260/502 R; 260/502 A
[58] Field of Search ......................... 260/502 R, 502 A

[56] References Cited

U.S. PATENT DOCUMENTS

| | | | |
|---|---|---|---|
| 2,814,641 | 11/1957 | Phillips et al. ................... | 260/502 R |
| 3,264,346 | 8/1966 | Weiberg ........................... | 260/502 R |
| 3,284,491 | 11/1966 | Karach et al. .................... | 260/502 R |

*Primary Examiner*—Werren B. Lone
*Attorney, Agent, or Firm*—Spencer & Kaye

[57] ABSTRACT

A continuous process for the manufacture of carboxylic peracids by reacting the corresponding carboxylic acid with hydrogen peroxide in the presence of a catalyst and in the presence of an inert organic liquid which is a solvent for the peracid and is capable of forming a heterogeneous azeotrope with water, removing the water present in the reaction mixture by distillation of the water/organic liquid azeotrope, and keeping sufficient water in the reaction mixture to allow the formation of an aqueous phase which is separate from an organic phase containing the organic liquid.

18 Claims, 1 Drawing Figure

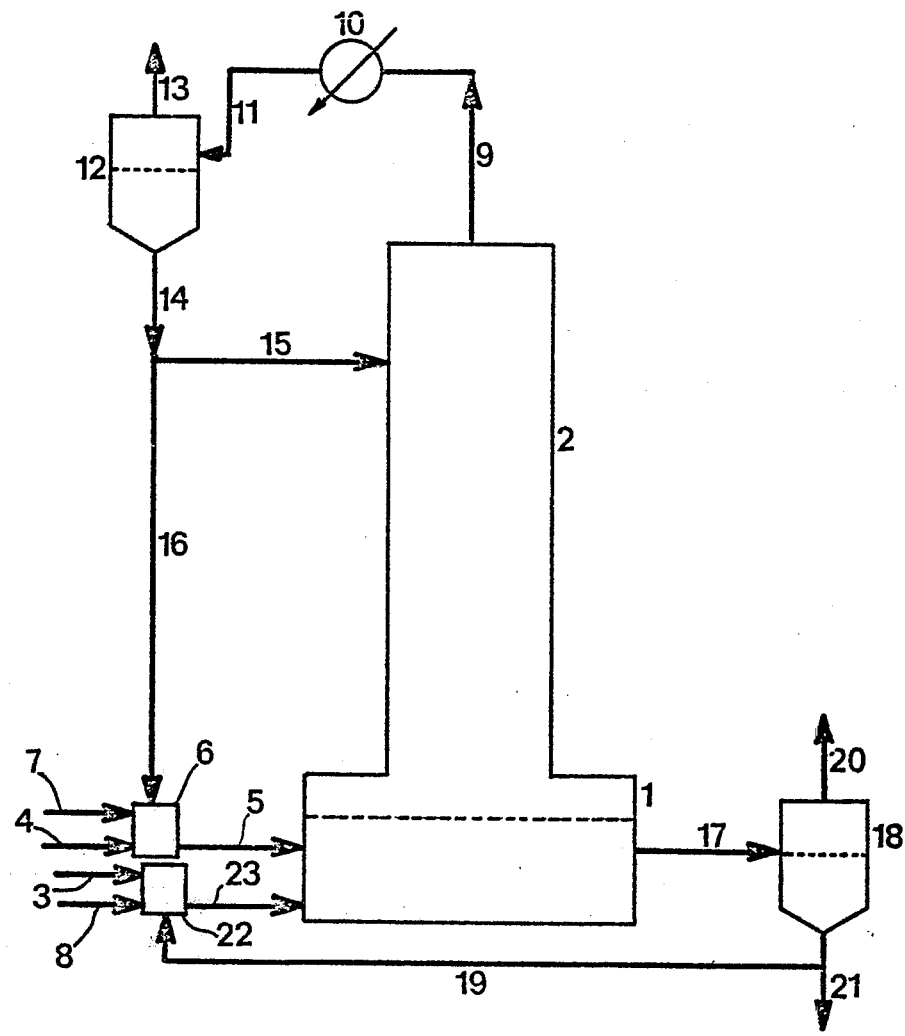

PROCESS FOR THE MANUFACTURE OF CARBOXYLIC PERACIDS

BACKGROUND OF THE INVENTION

The present invention relates to a continuous process for the manufacture of carboxylic peracids by reaction of the corresponding carboxylic acids with hydrogen peroxide in the presence of a catalyst.

It is known to manufacture carboxylic peracids by reacting the corresponding carboxylic acid with hydrogen peroxide, generally employed in the form of an aqueous solution, in the presence of small amounts of a catalyst such as sulphuric acid. This reaction gives rise to the formation of water. In order to obtain the carboxylic peracid directly in the anhydrous form, it has been proposed, in U.S. Pat. No. 2,814,641 issued to Phillips et al on Nov. 26, 1957, to carry out the reaction in the presence of a solvent which is capable of forming a minimum boiling-point azeotrope with water, and to remove the water formed by the reaction, and also the water for dilution of the reactants, by distillation of this azeotrope.

This known process exhibits certain serious disadvantages. In fact, the proportion of peroxide compounds (hydrogen peroxide and carboxylic peracid) persent in the reaction mixture is very large and increases as the reaction and the azeotropic distillation proceed. This involves risks of explosion which make the reaction particularly difficult to carry out. Furthermore, in this known process, the catalyst is present in the organic solution of peracid at the end of the process and it is therefore necessary to provide for the removal of this catalyst. This removal is extremely difficult to carry out. Furthermore, the presence of spent catalyst in the organic solution of peracid proves very inconvenient for all the subsequent uses of this solution, such as its use as an epoxidizing agent. Moreover, this process involves a high consumption of catalyst which cannot be recovered. Thus, in order to limit the disadvantages associated with the presence of the catalyst in the organic solution of peracid, it is necessary to use small relative amounts of catalyst, which generally do not exceed 5% of the weight of carboxylic acid employed, and this has the adverse consequence of substantially reducing the reaction rates. Finally, since the reaction for the formation of the peracid takes place mainly in the aqueous phase and, furthermore, since this aqueous phase is removed by azeotropic distillation, the rate of production of the peracid decreases very substantially with time as the aqueous phase disappears. In order to achieve high degrees of conversion, it is therefore appropriate to use very long reaction times. Thus, it is only with great difficulty that this known process can be carried out in installations which operate continuously.

SUMMARY OF THE INVENTION

It is an object of the present invention to provide a novel process which can very easily be carried out continuously and which does not exhibit the above-mentioned disadvantages.

The present invention therefore relates to a continuous process for the manufacture of carboxylic peracids by reaction of the corresponding carboxylic acid with hydrogen peroxide in the presence of a catalyst and in the presence of an inert organic liquid which is a solvent for the peracid and is capable of forming a heterogeneous azeotrope with water, in which process water present in the reaction mixture is removed by distillation of the water/organic liquid azeotrope, and in which a sufficient amount of water is kept in the reaction mixture to allow the formation of an aqueous phase which is separate from an organic phase containing the organic liquid.

In general, the amount of water kept in the reaction mixture is sufficient for the weight ratio of the aqueous phase to the organic phase, in the reaction mixture, to be more than 0.05. Preferably, this ratio is more than 0.1. The best results are obtained when this ratio is more than 0.2.

Furthermore, in most cases, it is of no value to keep amounts of water in the reaction mixture which are such that the weight ratio of the aqueous phase to the organic phase is more than 20. Preferably, this ratio is less than 10. The best results are obtained when it is less than 5.

The aqueous phase generally comprises from 5 to 95%, and most frequently from 10 to 70%, by weight, of water, the remainder substantially consisting of the constituents of the reaction mixture and mainly of the hydrogen peroxide and the catalyst when the latter is soluble and is not in the form of a solid suspension. It also generally comprises part of the carboxylic acid and part of the carboxylic peracid.

The water present in the aqueous phase can originate, in particular, from the reaction or from the introduction of certain constituents of the reaction mixture, in general the hydrogen peroxide and, if appropriate, the catalyst in the form of aqueous solutions. It may also have been added intentionally.

The organic phase generally comprises from 30 to 98%, and most frequently from 40 to 95%, by weight, of organic liquid, the remainder substantially consisting of constituents of the reaction mixture and mainly of the carboxylic acid and the carboxylic peracid.

It can also contain small amounts of hydrogen peroxide and, if appropriate, small amounts of catalyst. In general, the proportion of hydrogen peroxide in the organic phase does not exceed 5% of its weight and the proportion of catalyst therein does not exceed 1% of its weight. Most frequently, the respective proportions of hydrogen peroxide and catalyst in the organic phase do not exceed 2 and 0.4% of its weight.

The organic liquid employed in the reaction mixture must be inert with respect to the various constituents of the reaction mixture under the reaction conditions. Moreover, it must be able to form, with water, a minimum boiling-point heterogeneous azeotrope of which the boiling-point, under the same pressure conditions, must be lower than the boiling-point of the other constituents and of the other possible azeotropes which could be formed in the reaction mixture.

Finally, it must dissolve the carboxylic peracid formed during the reaction and preferably to such an extent that, under the reaction conditions, the concentration of the peracid in the organic phase, expressed in mols per liter, is equal to at least 0.05, and preferably at least 0.2, times the concentration of the peracid in the aqueous phase.

According to a preferred embodiment of the process according to the invention, part of the reaction mixture is withdrawn continuously and the aqueous phase is separated from the organic phase, by decantation, in the part which has been withdrawn. Preferably, the aqueous phase separated in this way is reintroduced into the reaction mixture. The organic phase separated in this way constitutes the product produced by the process.

This embodiment is particularly advantageous when employing an organic liquid which is very slightly soluble in water and in which water is slightly soluble. Preferably, the organic liquid chosen is such that the proportion of water in the organic phase is less than the proportion of water in the water/organic liquid azeotrope, under the same temperature and pressure conditions; most frequently, it is chosen so that the amount of water in the organic phase is less than 5% and preferably less than 1%. On the other hand, the amount of organic liquid dissolved in the aqueous phase is less critical; in general, the organic liquid is chosen so as to ensure that this amount does not exceed 10% and most frequently 5%. Moreover, the organic liquid chosen is such that the densities of the aqueous and organic phases are sufficiently different to permit their separation by decantation.

According to a variant, which is also preferred, of the above-mentioned embodiment, the organic phase obtained by decantation is used, without prior separation into its main constituents, for the manufacture of epoxides from olefins, in accordance with processes which are in themselves well known.

This organic phase contains variable amounts of carboxylic peracid, which are generally between 5 and 40% by weight. Before being employed for epoxidation, it can be subjected to various treatments, for example in order to remove the final traces of moisture and catalyst. However, these treatments are not essential. During the epoxidation reaction, the molar ratio of the carboxylic peracid to the olefin which is to be epoxidized is generally between 0.01 and 20. It is preferably between 0.1 and 10. It is also possible to add to the reaction mixture small amounts of various additives such as polymerization inhibitors, stabilizers for the peracid, or sequestering agents.

The epoxidation reaction is generally carried out at temperatures between 0° and 150° C. These temperatures are preferable between 15° and 120° C. The reaction pressure is generally sufficient to maintain at least one liquid phase. It is generally between 0.05 and 80 kg/cm$^2$. Of course, the reaction temperature and pressure depend on the particular nature of the olefin which is to be epoxidized. Thus, in order to epoxidize propylene, a temperature of 20° to 100° C. and a pressure of 0.8 to 30 kg/cm$^2$ are most frequently used. In order to epoxidize allyl chloride and allyl alcohol, a temperature of 20° to 150° C. and a pressure of 0.1 to 10 kg/cm$^2$ are most frequently used. The reactors used for carrying out the epoxidation reaction are generally reactors which facilitate heat exchange so as to permit a better control of the reaction temperatures. Tubular reactors or autoclaves, a single reactor or reactors in cascades can thus be used.

The reaction mixture obtained by epoxidation consists essentially of the organic liquid, olefin oxide, carboxylic acid and unconverted reactants; it may contain small amounts of by-products and small amounts of various additives. It is usually subjected to a first separation so as to recover, on the one hand, the unconverted olefin, and, on the other hand, a first organic solution consisting essentially of organic liquid, the olefin oxide, carboxylic acid and, possibly, unconverted carboxylic peracid.

In the case of volatile olefins, for example, propylene, this separation is advantageously carried out by a simple rapid reduction in pressure to atmospheric pressure. In the case of less volatile olefins, for example allyl chloride or allyl alcohol, this first separation can be carried out by distillation. The olefin collected is advantageously recycled to the epoxidation reaction. In order to do this, the olefin can be absorbed in the gaseous form in the organic phase containing the peracid, before sending it to the epoxidation reaction. It is also possible to condense the olefin and then simply to send it to the epoxidation reaction.

The first organic solution collected from the first separation is usually subjected to a second separation, advantageously by distillation, so as to recover, on the one hand, the desired olefin oxide, and, on the other hand, a second organic solution of carboxylic acid in the organic liquid. The olefin oxide can be used as obtained or can be subjected to certain subsequent purification steps in order to remove therefrom the possible traces of by-products such as aldehydes.

According to the variant which is now being described, the solution of carboxylic acid in the organic liquid, which may additionally contain the unconverted carboxylic peracid and also certain by-products and additives such as those mentioned above, is returned directly to the manufacture of the peracid. This solution is advantageously pre-heated before being introduced into the reaction zone, so as to provide at least part of the heat required for the azeotropic distillation.

When using this preferred variant, the organic liquid is chosen from amongst those of which the boiling-point is higher than the boiling-point of the olefin and the olefin oxide. Furthermore, the organic liquid should not form an azeotrope with the olefin and the olefin oxide. Finally, in the case where the organic liquid is capable of forming an azeotrope with the carboxylic acid or the carboxylic peracid, the boiling-points of these azeotropes should be higher than those of the olefin and the olefin oxide.

Any organic compound which is liquid under the reaction conditions corresponding to the conditions defined above can be suitable for carrying out the process according to the invention. These liquids are generally chosen from amongst carboxylic acid esters, ethers, halogenated hydrocarbons, unsubstituted hydrocarbons, hydrocarbons substituted by nitro groups, non-acidic esters of nitric acid, carbonic acid and phosphoric acid, and mixtures thereof.

As carboxylic acid esters which are generally very suitable, there may be mentioned aliphatic, alicyclic or aromatic esters of mono- or poly-carboxylic acids with mono- or poly-hydric alcohols containing from 4 to 20, and preferably from 4 to 10, carbon atoms in the molecule. Amongst these carboxylic acid esters, those which are particularly suitable are isopropyl, propyl, butyl, isobutyl, sec.-butyl, tert.-butyl, amyl, isoamyl and sec.-amyl formates and acetates, methyl, ethyl, propyl, isopropyl, butyl, isobutyl and isoamyl mono- and di-chloroacetates, propionates, butyrates and isobutyrates, methyl, ethyl and propyl valerates, isovalerates and caproates, methoxyethyl, ethoxyethyl and cyclohexyl acetates, methyl pivalate and the diethyl esters of phthalic acid and adipic acid.

As ethers which are generally very suitable, there may be mentioned symmetric or asymmetric aliphatic ethers containing from 4 to 12 carbon atoms, such as 2,2'-dichlorodiethyl ether, butyl ethyl ether, tert.-butyl ethyl ether, tert.-amyl methyl ether, diisopropyl ether, dipropyl ether, dibutyl ether, ethyl hexyl ether and diisobutyl ether.

As halogenated hydrocarbons which are generally very suitable, there may be mentioned aromatic, aliphatic and alicyclic halogenated hydrocarbons which contain from 1 to 8 carbon atoms in their molecule and are substituted by at least one halogen which is preferably chosen from amongst chlorine fluorine and bromine. Particularly suitable halogenated hydrocarbons are carbon tetrachloride, chloroform, methylene chloride, di-, tri-, tetra- and penta-chloroethanes, trichlorotrifluoroethanes, tri- and tetra-chloroethylene, mono-, di- and tri-chloropropanes, monochloro- or polychlorobutanes, -methylpropanes, -pentanes and -hexanes, mono- and di-chlorobenzenes and chlorotoluenes.

As hydrocarbons substituted by nitro groups which are generally very suitable, there may be mentioned aromatic, aliphatic or alicyclic hydrocarbons containing from 3 to 8 carbon atoms, such as nitropropanes, nitrobenzene and nitrocyclohexane.

As unsubstituted hydrocarbons which are generally very suitable, there may be mentioned aliphatic, aromatic or alicyclic hydrocarbons containing from 5 to 14 carbon atoms, such as benzene, toluene, xylene, pentane, hexane heptane, octane, diisobutyl, cyclohexane, methylcyclohexane and tetralin.

As carbonic acid esters which are generally very suitable, there may be mentioned aliphatic esters containing from 3 to 9 carbon atoms in the molecule, such as dimethyl, diethyl, diisobutyl, dibutyl, di-tert.-butyl, dipropyl and diisopropyl carbonates. Nitric acid esters which are generally very suitable are those chosen from amongst aliphatic esters containing from 1 to 5 carbon atoms in the molecule, such as methyl, propyl, butyl and isoamyl nitrates. Phosphoric acid esters which are very suitable are those which correspond to the formula

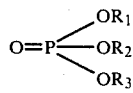

in which $R_1$, $R_2$ and $R_3$ are identical or different and represent alkyl, aryl, arylalkyl or alkylaryl groups which are such that the molecule contains from 3 to 30 carbon atoms. Trimethyl, tributyl, trioctyl and dioctyl phenyl phosphates may be mentioned as examples of particular phosphates.

Organic liquids which are particularly suitable for use in the manufacture of peracetic acid and perpropionic acid are benzene, toluene, 1,2-dichloropropane, 1,1,2,2-tetrachloroethane, pentachloroethane, tetrachloroethylene, 1-nitropropane, chlorobenzene, parachlorotoluene, methyl chloroacetate, diethyl carbonate, dichloroethane, butyl acetate, cyclohexane and tributyl phosphate. Particularly good results are obtained with 1,2-dichloropropane, 1,2-dichloroethane, 1,1,2,2-tetrachloroethane and mixtures thereof.

The azeotrope collected by distillation is generally condensed and separated by decantation, so as to separate the water from the organic liquid. The organic liquid thus collected can advantageously be used, at least in part, for ensuring reflux in the distillation zone. It can also be reintroduced, in general after vaporization, into the reaction zone in order to serve the purpose of forming the organic phase. This introduction in the form of a vapor makes it possible to provide a least part of the heat required for the vaporization of the water-/organic liquid azeotrope.

The process of the invention can be applied to the manufacture of a large number of carboxylic peracids. Thus, it can be used for forming peracids starting from mono- or poly-carboxylic acids. In the latter case, the polycarboxylic acid can also be employed in the form of the corresponding anhydride in the process according to the invention. The process according to the invention is particularly suitable for the production of peracids from carboxylic acids containing from 1 to 10 carbon atoms, such as aliphatic, alicyclic or aromatic carboxylic acids, for example formic acid, acetic acid, chloroacetic acids, propionic acid, butanoic acid, maleic acid or maleic anhydride, benzoic acid, cyclohexanecarboxylic acid and phthalic acids and phthalic anhydride. Particularly advantageous results are obtained when manufacturing peracetic acid and perpropionic acid starting from acetic acid and propionic acid, respectively.

The catalyst employed is generally an acid catalyst which is suitable for esterification reactions, such as, for example, sulphuric acid, alkyl-, aryl-, arylalkyl- and alkylaryl-sulphonic acids, phosphoric acid, alkyl, aryl, alkylaryl and arylalkyl acid phosphates, trifluoroacetic acid, acetylsulphoacetic acid and also ion exchange resins of the sulphonated polymer or copolymer type. Preferred catalysts which may be mentioned more particularly are sulphuric acid and methane-, ethane-, benzene-, toluene-, xylene-, butane-, propane- and naphthalene-sulphonic acids. Amongst these catalysts, it is preferred to use those which are soluble in water and are insoluble or sparingly soluble in the organic liquid. The best results are obtained with the water-soluble catalysts of which the concentration in the organic phase is less than 3%, and preferably less than 1%, by weight, under the reaction conditions. Particularly advantageous results have been obtained with sulphuric acid.

The concentration of catalyst in the reaction mixture can vary within wide proportions. In order to obtain fast reaction rates, high concentrations of catalysts are generally used. The amount of catalyst used is generally more than 5% of the total weight of carboxylic acid and carboxylic peracid present in the reaction mixture. The proportion by weight of catalyst is preferably between 0.1 and 30 times the total weight of carboxylic acid and carboxylic peracid present in the reaction mixture. The best results are obtained when this proportion is between 0.2 and 10 times the total weight of carboxylic acid and carboxylic peracid.

The catalyst can be employed in the pure state. However, it is advantageously employed in the form of an aqueous solution if it is soluble in water. In this case, the catalyst can advantageously be employed by reintroducing, into the reaction mixture, the aqueous phase originating from the separation of the latter by decantation, after having added an additional amount of catalyst if necessary. In general, the concentration of water-soluble catalyst in the aqueous phase is between 10 and 60% by weight.

The carboxylic acid can be employed in the pure state in the process according to the invention. However, it is generally employed in the form of a solution in the organic liquid. Such solutions containing from 2 to 70%, and preferably from 5 to 60%, by weight of carboxylic acid are advantageously introduced into the reaction mixture. In order to prepare these solutions, it is possible to use organic liquid originating from the separation of the distilled azeotrope by decantation, fresh organic liquid or also organic liquid which has been recovered after using the organic solution of peracid.

The hydrogen peroxide used for the reaction can be employed either in the pure state or in the form of aqueous solutions.

The hydrogen peroxide can particularly be employed in the form of an aqueous solution. Concentrated solutions of hydrogen peroxide, containing from 20 to 90% by weight of hydrogen peroxide, are advantageously used. Other concentrations can also be suitable but are less favorable. In fact, at lower concentrations of hydrogen peroxide, the amounts of water to be removed by azeotropic distillation are very large, whereas solutions which are more highly concentrated in hydrogen peroxide are difficult to produce industrially.

The proportions of reactants in the reaction mixture can vary within wide limits, in absolute terms and relative to one another, depending especially on the chosen rates of introduction of the reactants. Thus, the amount of hydrogen peroxide is generally between 0.1 and 10, and preferably between 0.2 and 5, mols per mol of carboxylic acid function. The most advantageous results are usually obtained when the amounts of hydrogen peroxide and carboxylic acid introduced into the reaction mixture are in a ratio which is close to, or slightly less than, the stoichiometric ratio. The hydrogen peroxide and the carboxylic acid are therefore preferably introduced in amounts such that between 0.2 and 2, and preferably between 0.4 and 1.2 mols of hydrogen peroxide are introduced per mol of carboxylic acid function.

The hydrogen peroxide can be introduced directly into the reactor or into the aqueous solution of catalyst sent to the reactor, when this catalyst is soluble in water. The hydrogen peroxide is advantageously introduced into the aqueous solution of catalyst sent to the reactor. The hydrogen peroxide is most frequently introduced into the aqueous phase which is collected by separation of the reaction mixture by decantation and is recycled continuously to the reactor. This introduction is advantageously carried out in stages so as to prevent the local concentrations of hydrogen peroxide from becoming too high. The flow rate of the continuously recycled aqueous phase must be sufficient for the composition of the resulting aqueous phase enriched in hydrogen peroxide to always be such that the reaction mixture remains outside the explosion limits.

The temperature of the reaction mixture is generally chosen to be below 100° C. and it is most frequently between 20° and 70° C. Higher temperatures are less valuable because they involve a risk of sudden decomposition of the peroxide compounds. The pressure is regulated as a function of the temperature, so as to maintain boiling. Thus, it can vary within a wide range. It is most frequently between 0.01 and 1.2 kg/cm$^2$.

The heat required to maintain boiling can be provided in accordance with conventional techniques which are in themselves known. Thus, it is possible to heat the reaction mixture (aqueous phase and organic phase) by bringing it into contact with an exchange surface heated by means of a heat-transfer fluid such as steam. It is also possible and advantageous to introduce the organic liquid, the carboxylic acid or also mixtures thereof into the reaction mixture in the form of vapor.

In order to carry out the process according to the invention, any apparatus which is suitable for liquid reaction mixtures can be used, in particular vat reactors equipped with a stirring system. More particularly, it is advantageous to use reactors, in themselves known, which make it possible to distil one of the constituents of a liquid reaction mixture during the reaction. In general, the reactors used make it possible to ensure intimate mixing of the aqueous and organic phases and a good exchange between the liquid phases and the gaseous phase, so as to assist the vaporization of the water-/organic liquid azeotrope.

These reactors are advantageously coupled to distillation columns which are in themselves known, such as plate columns or packed columns.

The various parts of the reactors and of the columns in contact with the reaction mixture are advantageously made of corrosion-resistant materials such as stainless steels, the alloys INCONEL, HASTELLOY, INCOLOY, NIMONIC, NI-RESIST and CHLORIMET, and enamelled steels.

The separation, by decantation, of the reaction mixture withdrawn from the reactor, and that of the water-/organic liquid azeotrope collected at the top of the column, can be carried out in accordance with various techniques which are in themselves known, such as separation by gravity or by the action of a centrifugal force, or passage through porous membranes which are selectively wetted by one or other of the phases. Various types of apparatuses which are in themselves known can be used for this purpose. Thus, it is possible to use florentine separators, centrifugal separators, separating filters with membranes, or electrical separators. The separation by decantation can be facilitated by a prior operation for coalescing the droplets in apparatuses which are in themselves known, such as pads or shells made of fibrous materials which can preferably be wetted by the disperse phase.

BRIEF DESCRIPTION OF THE DRAWING

The process according to the invention can be carried out continuously in an apparatus such as that shown schematically in the single FIGURE of the attached drawing, which is a simplified elevational view of a particular practical embodiment of apparatus for practicing the invention.

DESCRIPTION OF THE PREFERRED EMBODIMENTS

Referring to the FIGURE, a concentrated solution of hydrogen peroxide and catalyst, obtained by mixing, in a mixer 22, aqueous hydrogen peroxide introduced via line 3 with catalyst introduced via line 8, is introduced via line 23 into a reactor 1 surmounted by a distillation column 2, and a solution of carboxylic acid in an organic liquid, obtained by mixing, in a mixer 6, the carboxylic acid being introduced via line 4 with the organic liquid introduced via line 7, is introduced via line 5 into the reactor 1.

In the course of the ensuing reaction, the water/organic liquid azeotrope leaves the distillation column 2 via line 9, is condensed in a condenser 10 and is sent via line 11 to a separator 12. If the organic liquid has a higher density than that of water, the water is collected via line 13 at the top of the separator and the organic liquid is collected via line 14 at the bottom of the separator; in the opposite case, the withdrawals are reversed. The organic liquid is recycled via line 15 to the distillation column, where it constitutes the reflux. In certain cases, part of this organic liquid can be sent via line 16 into the mixer 6, where it acts as a solvent for carboxylic acid.

Part of the reaction mixture is withdrawn continuously from the mixer reactor via line 17 and is sent to a separator 18. If the density of the organic phase is lower than that of the aqueous phase, the organic phase, which contains the carboxylic peracid produced, is withdrawn at the top of the separator 18, via line 20, and the aqueous phase, which is recycled to the reactor via line 19, is withdrawn at the bottom of the separator 18. A bleed 21 makes it possible to remove some of the by-products which build up in the aqueous phase. The organic phase collected via line 20 can be directly used as obtained, especially for carrying out epoxidation reactions, or it can also be subjected to purification treatments for removing therefrom the final traces of moisture or catalyst.

The process according to the invention proves particularly valuable because it makes it possible to obtain continuously organic solutions which are essentially anhydrous and have a high concentration of carboxylic peracid. Moreover, the explosion risks due to the decomposition of the peroxide compounds in the reaction medium are greatly reduced because the total concentration of peroxide compounds is kept at a constant level and because points of concentration of peroxide compounds are never observed. The total proportion of peroxide compounds in the reaction mixture remains permanently at a relatively low level. Furthermore, the degree of conversion of the reactants is excellent. Similarly, the process does not entail the destruction of the catalyst and does not require any complicated process for the recovery of the catalyst and, in particular, it does not require any distillation. Finally, the process makes it possible to choose reaction conditions which enable remarkably fast reaction rates to be achieved.

The carboxylic peracids obtained in accordance with the process of the present invention can be used as a source of active oxygen in numerous chemical reactions and more particularly for the manufacture of epoxides from olefins. For this purpose, any optionally substituted organic compound can be employed which contains at least one unsaturated carbon-carbon bond and which more particularly contains from 2 to 20 carbon atoms in its molecule. Examples of such olefins which may be mentioned are propylene, allyl chloride, allyl alcohol and styrene.

In order to illustrate the invention, without thereby limiting its scope, an example of the manufacture of a carboxylic peracid is given below.

EXAMPLE

The apparatus used is similar to that represented schematically in the FIGURE.

The reactor, which has a capacity of 1 liter, initially contains 0.2 kg of 45% strength sulphuric acid.

The temperature of the reactor is maintained at about 39° C. and the pressure therein is about 100 mm of mercury.

0.12 kg per hour of a 70% strength by weight aqueous solution of hydrogen peroxide and 1.07 kg per hour of a 27% strength by weight solution of propionic acid in 1,2-dichloropropane are introduced continuously into the reactor.

The weight ratio of the aqueous phase to the organic phase present in the reactor is 1.04. A stirring system keeps the aqueous phase and the organic phase as an emulsion.

Part of the reaction mixture is withdrawn continuously. After separation of the withdrawn fraction by decantation 1.11 kg per hour of an organic solution having the following composition:

|  | g/kg |
| --- | --- |
| perpropionic acid | 200 |
| propionic acid | 92.2 |
| hydrogen peroxide | 2.89 |
| water | traces |
| sulphuric acid | 1.27 |
| 1,2-dichloropropane | 703.64 | are obtained.

An examination of the results obtained in the example shows that it is possible, by using the process of the invention, to obtain organic solutions having high concentrations (20%) of perpropionic acid which is virtually free from water and catalyst.

The concentrated organic solution obtained in this way can be used directly, for example in order to epoxidize propylene. A solution of propylene oxide in 1,2-dichloropropane, additionally containing propionic acid and unreacted propylene, is thus collected. A first distillation of this solution makes it possible to collect the unreacted propylene at the top of the column. A second distillation yields propylene oxide at the top of the column and a solution of propionic acid in 1,2-dichloropropane at the bottom. This solution can be used directly for carrying out the reaction for the manufacture of perpropionic acid.

It will be understood that the above description of the present invention is susceptible to various modifications, changes and adaptations, and the same are intended to be comprehended within the meaning and range of equivalents of the appended claims.

What is claimed is:

1. In a continuous process for the manufacture of a carboxylic peracid by reaction, in a reaction mixture and under reaction conditions sufficient to produce said carboxylic peracid, of the corresponding carboxylic acid with hydrogen peroxide in the presence of a catalyst and in the presence of an inert organic liquid which is contained in an organic phase and is a solvent for the peracid and is capable of forming a heterogeneous azeotrope with water, which process includes removing water present in the reaction mixture by distillation of the water/organic liquid azeotrope, the improvement comprising maintaining a sufficient amount of water in the reaction mixture to allow the formation of an aqueous phase which is separate from the organic phase containing the organic liquid, the weight ratio of the aqueous phase to the organic phase in the reaction mixture being more than 0.05.

2. Process according to claim 1, wherein the weight ratio of the aqueous phase to the organic phase, in the reaction mixture, is more than 0.1 and less than 10.

3. Process according to claim 1 or 2, further comprising withdrawing part of the reaction mixture, and then separating the aqueous phase from the organic phase, by decantation, of the part which has been withdrawn.

4. Process according to claim 3, further comprising reintroducing the separated aqueous phase into the reaction mixture.

5. Process according to claim 1 or 2 wherein the organic liquid has a composition such that the solubility of water in the organic phase is less than the proportion of water in the water/organic liquid azeotrope.

6. Process according to claim 1 or 2 wherein the amount of catalyst present in the reaction mixture is between 0.1 and 30 times the total weight of carboxylic acid and carboxylic peracid.

7. Process according to claim 1 or 2 wherein the organic liquid is chosen from among carboxylic acid esters, ethers, halogenohydrocarbons, unsubstituted hydrocarbons, hydrocarbons substituted by nitro groups, and non-acidic esters of nitric, phosphoric and carbonic acids.

8. Process according to claim 1 or 2 wherein the carboxylic acid is propionic acid or acetic acid.

9. Process according to claim 1 or 2 wherein the catalyst is chosen from among sulphuric acid, alkyl-, aryl-, arylalkyl- and alkylaryl-sulphonic acids, phosphoric acid, alkyl, aryl, alkylaryl and arylaklyl acid phosphates, trifluoroacetic acid, acetyl-sulphoacetic acid and sulphonated ion exchange resins.

10. Process according to claim 1 or 2 wherein the organic liquid is chosen from among 1,2-dichloropropane and 1,2-dichloroethane, the carboxylic acid is propionic acid and the catalyst is sulphuric acid.

11. Process according to claim 1, wherein an aqueous solution containing hydrogen peroxide and said carboxylic acid in a ratio between 0.1 to 10 moles of hydrogen peroxide per mole of carboxylic acid is continuously introduced into said reaction mixture;

said catalyst being maintained in said reaction mixture in an amount greater than 5% of the total weight of said carboxylic acid and said carboxylic peracid in said reaction mixture; and the reaction mixture is maintained at a temperature below 100° C. and at a pressure of between 0.01 and 1.2 kg/cm$^2$.

12. Process according to claim 1, wherein said weight ratio is no greater than 20.

13. Process according to claim 1, wherein said weight ratio is more than 0.1.

14. Process according to claim 12, wherein said weight ratio is no greater than 10.

15. Process according to claim 1, wherein said weight ratio is more than 0.2.

16. Process according to claim 15, wherein said weight ratio is less than 10.

17. Process according to claim 16, wherein said weight ratio is less than 5.

18. Process according to claim 1 or 2, further comprising withdrawing part of the reaction mixture, and then separating the aqueous phase from the organic phase of the part which has been withdrawn.

* * * * *